United States Patent
Chen et al.

(10) Patent No.: US 10,645,501 B1
(45) Date of Patent: May 5, 2020

(54) SYSTEMS AND METHODS FOR EMULATING A REMOTE LISTENING ENVIRONMENT FOR A RECIPIENT OF A COCHLEAR IMPLANT SYSTEM

(71) Applicant: Advanced Bionics AG, Staefa (CH)

(72) Inventors: Chen Chen, Valencia, CA (US); Leonid M. Litvak, Los Angeles, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 16/289,484

(22) Filed: Feb. 28, 2019

(51) Int. Cl.
*H04R 25/00* (2006.01)
*A61N 1/36* (2006.01)

(52) U.S. Cl.
CPC ......... *H04R 25/30* (2013.01); *A61N 1/36039* (2017.08); *H04R 25/505* (2013.01); *H04R 2225/67* (2013.01)

(58) Field of Classification Search
CPC .. H04R 25/30; H04R 25/505; H04R 2225/67; A61N 1/36039
See application file for complete search history.

(56) References Cited

U.S. PATENT DOCUMENTS

| 9,761,223 B2 | 9/2017 | Blommer et al. | |
| 2012/0183165 A1* | 7/2012 | Foo | H04R 25/50 381/314 |

FOREIGN PATENT DOCUMENTS

| WO | 2017052574 | 3/2017 |
| WO | 2017052588 | 3/2017 |

OTHER PUBLICATIONS

Brook, et al., Developing a Mobile Audiometric Sound Booth Application for Apple IOS Devices, Edith Cowan University, 2nd Australian eHealth Informatics and Security Conference, Dec. 2-4, 2013.

De Graaff, et al., Assessment of speech recognition abilities in quiet and in noise: a comparison between self-administered home testing and testing in the clinic for adult cochlear implant users, International Journal of Audiology, Published online Sep. 27, 2018.

(Continued)

*Primary Examiner* — Andrew L Sniezek
(74) *Attorney, Agent, or Firm* — ALG Intellectual Property, LLC

(57) ABSTRACT

An exemplary emulation system may acoustically isolate the recipient from the local listening environment by disabling a microphone included in the cochlear implant system, receive user input representative of a request to present a sound token to the recipient, generate a modified sound token, and present the modified sound token to the recipient while the microphone is disabled. The modified sound token may be generated by adding a system noise floor of the cochlear implant system to the sound token. Additionally or alternatively, the modified sound token may be generated by adding an environmental noise floor of the remote listening environment to the sound token. Additionally or alternatively, the modified sound token may be generated by filtering the sound token with an acoustic transfer function of the remote listening environment.

13 Claims, 8 Drawing Sheets

(56) References Cited

OTHER PUBLICATIONS

De Graaff, et al., The Development of Remote Speech Recognition Tests for Adult Cochlear Implant Users: The Effect of Presentation Mode of the Noise and a Reliable Method to Deliver Sound in Home Environments, Audiology and Neurotology, 21(Suppl. 1), pp. 48-54, published online Nov. 3, 2016.

Iglehart, Speech perception in classroom acoustics by children with cochlear implants and with typical hearing, American Journal of Audiology, vol. 25, pp. 100-109, Jun. 2016.

Kidd, et al., The role of reverberation in release from masking due to spatial separation of sources for speech identification, Acta acustica united with acustica, vol. 91, pp. 526-536, Feb. 5, 2004.

Kokkinakis, et al., A channel-selection criterion for suppressing reverberation in cochlear implants, The Journal of the Acoustical Society of America, 129(5), May 2011, pp. 3221-3232.

Myhrum, et al., The Norwegian Hearing in Noise Test for Children, Ear & Hearing, vol. 37(1), pp. 80-92, Received Jan. 21, 2014; accepted Jul. 31, 2015.

Poissant, et al., Effects of reverberation and masking on speech intelligibility in cochlear implant simulations, The Journal of the Acoustical Society of America, vol. 119(3), Mar. 2006, pp. 1606-1615.

\* cited by examiner

SYSTEMS AND METHODS FOR EMULATING A REMOTE LISTENING ENVIRONMENT FOR A RECIPIENT OF A COCHLEAR IMPLANT SYSTEM

BACKGROUND INFORMATION

Hearing evaluations (e.g., hearing threshold tests, speech intelligibility tests, etc.) for cochlear implant recipients are typically done in an audiometric sound booth in a clinic. This requires the recipients to come in to the clinic, which may be inconvenient and/or difficult for many due to distance and/or cost. Moreover, sound booth availability at some clinics is often limited due to the high number of people serviced by these clinics.

Accordingly, it would be desirable to be able to perform hearing evaluations for cochlear implant recipients in non-sound booth settings. For example, it would be desirable for a cochlear implant recipient to be able to perform a self-evaluation of his or her hearing while the recipient is in his or her home. In these scenarios, sound tokens (e.g., audio used to perform the hearing evaluations) could be input directly into a direct audio input of a sound processor included in a cochlear implant system.

To be considered a viable alternative to in-clinic evaluations, remote evaluations should yield results that are substantially equivalent to those that would be achieved in a sound booth of a clinic. Unfortunately, due to a variety of factors, such substantial equivalency has heretofore been impossible to achieve.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
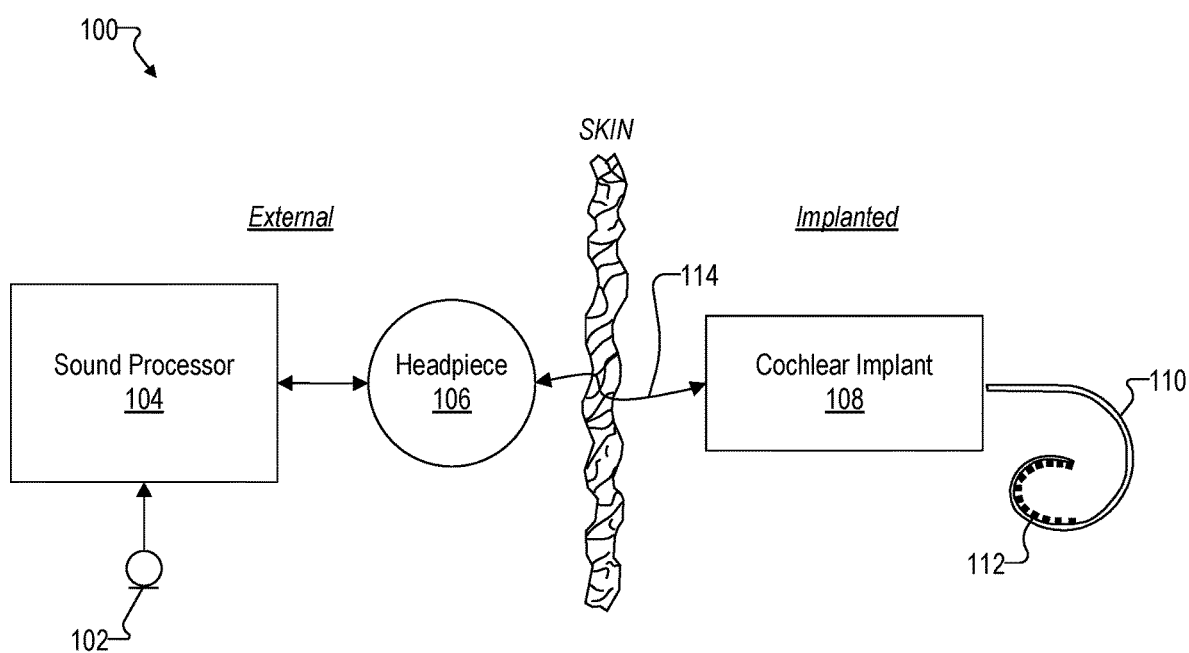
FIG. 1 illustrates an exemplary cochlear implant system according to principles described herein.

Systems and methods for emulating a remote listening environment that is physically remote from a local listening environment in which a recipient of a cochlear implant system is located are described herein. As will be described herein, an exemplary emulation system may acoustically isolate the recipient from the local listening environment by disabling a microphone included in the cochlear implant system, receive user input representative of a request to present a sound token to the recipient, generate a modified sound token, and present the modified sound token to the recipient while the microphone is disabled.

In some examples, the modified sound token may be generated by adding a system noise floor of the cochlear implant system (e.g., a microphone noise floor of the microphone) to the sound token. Additionally or alternatively, the modified sound token may be generated by adding an environmental noise floor of the remote listening environment to the sound token. Additionally or alternatively, the modified sound token may be generated by filtering the sound token with an acoustic transfer function of the remote listening environment. Each of these ways in which the modified sound token may be generated are described in more detail herein.

One example of a remote listening environment that may be emulated for a recipient of a cochlear implant system is a sound booth in which hearing evaluations for cochlear implant recipients are performed. In this example, it may be desirable to present a sound token (e.g., audio content represented by an audio file) to the recipient and perform a hearing threshold test, a speech intelligibility test, an audibility test, an audiogram, and/or any other hearing evaluation for the recipient based on the sound token. The sound token may be presented to the recipient by delivering the sound token directly to a sound processor included in the recipient's cochlear implant system. This may be performed in a variety of different ways. For example, a computing device (e.g., a personal computer, a smartphone, etc.) may be connected to the sound processor by plugging an audio cable into both the computing device and a direct audio input port of the sound processor. In this scenario, the sound token may be transmitted from the computing device to the sound processor by way of the audio cable. As another example, the computing device may be connected to the sound processor by way of a wireless connection (e.g., Bluetooth, a telecoil or FM system, etc.). In this scenario, the sound token may be wirelessly streamed from the computing device to the sound processor by way of the wireless connection.

As mentioned, regardless of how the sound token is directly delivered to the sound processor of the recipient's cochlear implant system, direct audio input of the sound token conventionally has yielded different hearing evaluation scores than scores achieved in a sound booth setting. One reason for this difference is that the microphone of the cochlear implant system is disabled during the direct audio input configuration. This prevents the noise floor of the cochlear implant system (e.g., the microphone and/or other components included in the cochlear implant system) from affecting the hearing evaluation score as it might while enabled in the sound booth setting. Another reason for this difference may be that in direct audio input configurations, the hearing evaluation scores are not affected by the noise floor and/or acoustics of the sound booth itself.

The systems and methods described herein may modify the sound token to achieve hearing evaluation scores that more accurately emulate hearing evaluation scores achieved in sound booth settings. For example, as described herein, the sound token may be modified by adding a system noise floor of the cochlear implant system to the sound token, adding a noise floor of the sound booth to the sound token, and/or filtering the sound token with an acoustic transfer function of the sound booth. As such, the systems and methods described herein may facilitate hearing evaluations of cochlear implant recipients in non-clinical settings and achieve hearing evaluation scores that are relatively close (e.g., substantially equivalent) to those that could be achieved in sound booths of clinics. This may improve the operation of a recipient's cochlear implant system, be more convenient for recipients and clinicians alike, and/or result in other benefits as described herein.

It will be recognized that remote environments other than sound booths may additionally or alternatively be emulated accordance with the systems and methods described herein. For example, a classroom, a church hall, a restaurant, and/or any other setting may be emulated in accordance with the systems and methods described herein.

FIG. 1 illustrates an exemplary cochlear implant system 100. As shown, cochlear implant system 100 may include a microphone 102, a sound processor 104, a headpiece 106 having a coil disposed therein, a cochlear implant 108, and an electrode lead 110. Electrode lead 110 may include an array of electrodes 112 disposed on a distal portion of electrode lead 110 and that are configured to be inserted into a cochlea of a recipient to stimulate the cochlea when the distal portion of electrode lead 110 is inserted into the cochlea. One or more other electrodes (e.g., including a ground electrode, not explicitly shown) may also be disposed on other parts of electrode lead 110 (e.g., on a proximal portion of electrode lead 110) to, for example, provide a current return path for stimulation current generated by electrodes 112 and to remain external to the cochlea after electrode lead 110 is inserted into the cochlea. As shown, electrode lead 110 may be pre-curved so as to properly fit within the spiral shape of the cochlea. Additional or alternative components may be included within cochlear implant system 100 as may serve a particular implementation.

As shown, cochlear implant system 100 may include various components configured to be located external to a recipient including, but not limited to, microphone 102, sound processor 104, and headpiece 106. Cochlear implant system 100 may further include various components configured to be implanted within the recipient including, but not limited to, cochlear implant 108 and electrode lead 110.

Microphone 102 may be configured to detect audio signals presented to the user. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal during normal operation by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, input by way of a clinician's programming interface (CPI) device, etc.) to one or more stimulation sites associated with an auditory pathway (e.g., the auditory nerve) of the recipient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may be housed within any suitable housing (e.g., a behind-the-ear ("BTE") unit, a body worn device, headpiece 106, and/or any other sound processing unit as may serve a particular implementation). In some examples, sound processor 104 is implemented by a bi-modal processor configured to direct cochlear implant 108 to apply electrical stimulation to a recipient and a loudspeaker (not shown) to apply acoustic stimulation to the recipient.

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108 (e.g., a wireless link between a coil disposed within headpiece 106 and a coil physically coupled to cochlear implant 108). It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the recipient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via communication link 114.

Cochlear implant 108 may include any suitable type of implantable stimulator. For example, cochlear implant 108 may be implemented by an implantable cochlear stimulator. Additionally or alternatively, cochlear implant 108 may include a brainstem implant and/or any other type of cochlear implant that may be implanted within a recipient and configured to apply stimulation to one or more stimulation sites located along an auditory pathway of a recipient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites (e.g., one or more intracochlear regions) within the recipient via electrodes 112 disposed along electrode lead 110. In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

Figure 2:
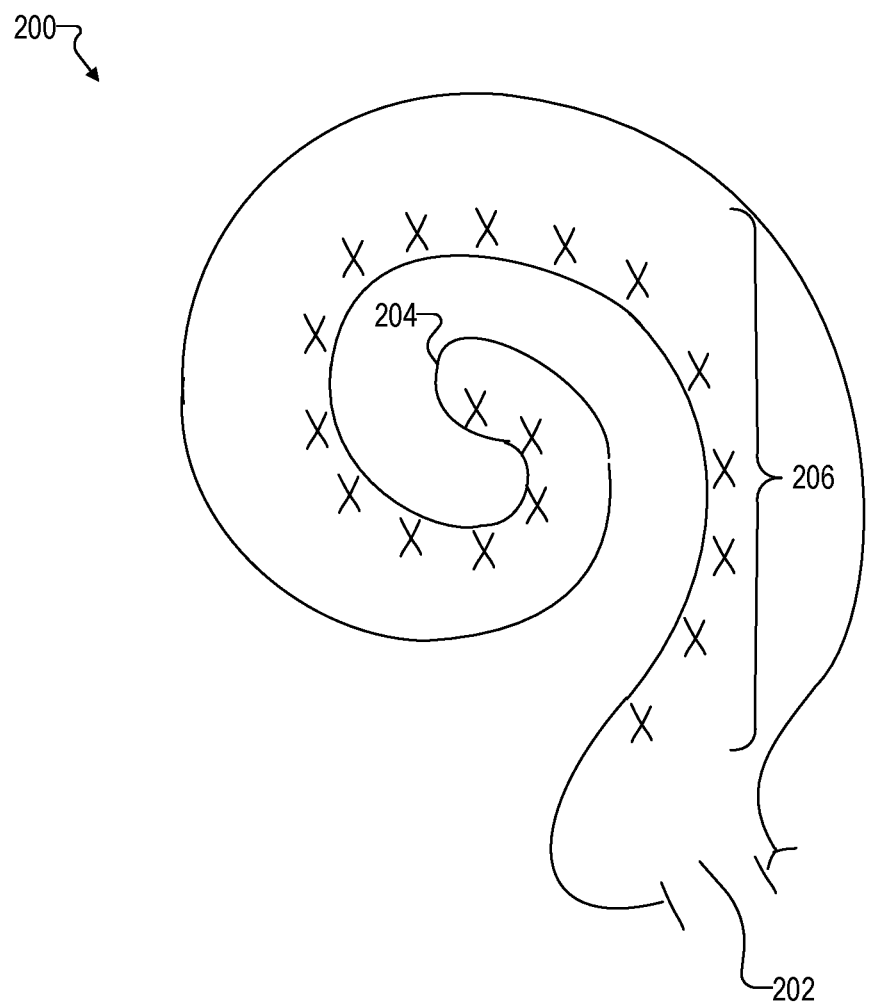
FIG. 2 illustrates a schematic structure of the human cochlea according to principles described herein.

FIG. 2 illustrates a schematic structure of the human cochlea 200 into which electrode lead 110 may be inserted. As shown in FIG. 2, cochlea 200 is in the shape of a spiral beginning at a base 202 and ending at an apex 204. Within cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, electrical stimulation applied by way of electrodes disposed within the apical region (i.e., "apical electrodes") may result in the recipient perceiving relatively low frequencies and electrical stimulation applied by way of electrodes disposed within the basal region (i.e., "basal electrodes") may result in the recipient perceiving relatively high frequencies. The delineation between the apical and basal electrodes on a particular electrode lead may vary depending on the insertion depth of the electrode lead, the anatomy of the recipient's cochlea, and/or any other factor as may serve a particular implementation.

In some examples, an emulation system separate from (i.e., not included within) cochlear implant system 100 may be selectively and communicatively coupled to sound processor 104 in order to perform one or more hearing evaluation operations with respect to a recipient of cochlear implant system 100. For example, the emulation system may present sound tokens to the recipient by way of cochlear implant system 100 in order to facilitate evaluation of how well cochlear implant system 100 is performing for the recipient.

Figure 3:
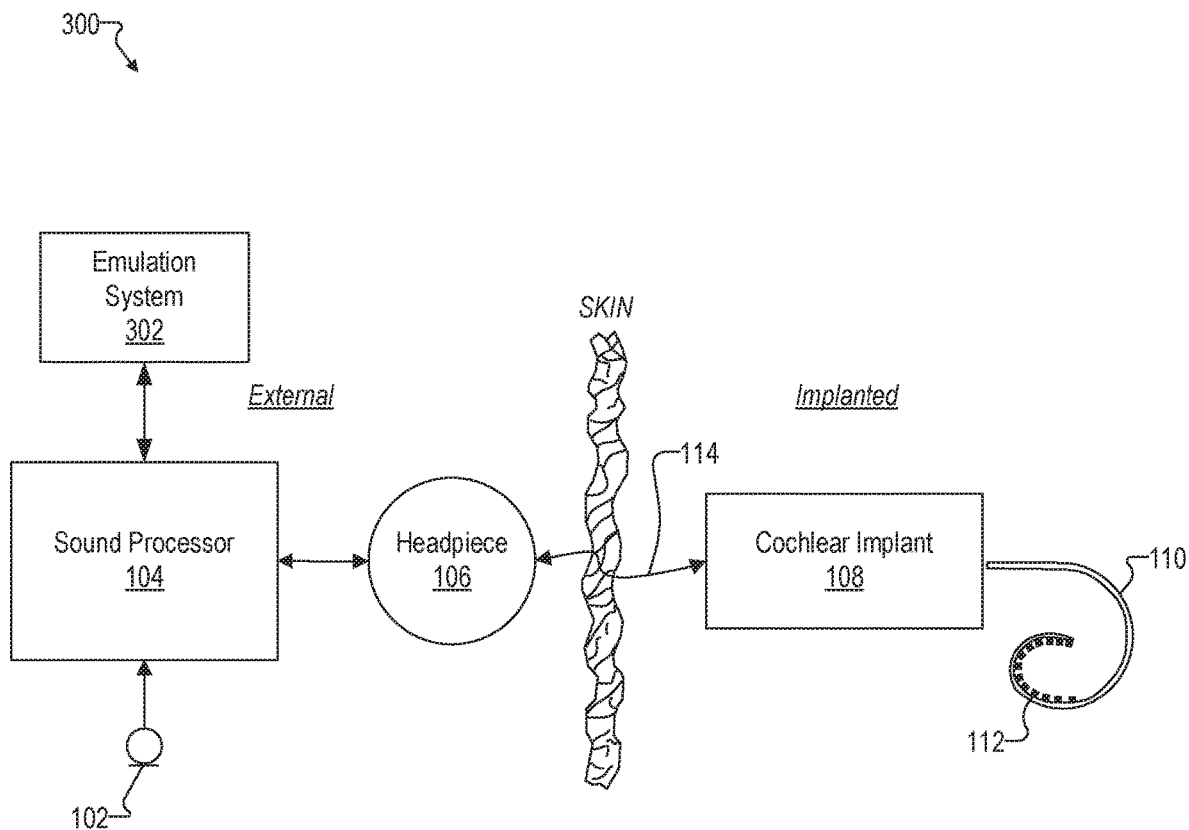
FIG. 3 illustrates an exemplary configuration in which an emulation system is communicatively coupled to a sound processor of a cochlear implant system according to principles described herein.

To illustrate, FIG. 3 shows an exemplary configuration 300 in which an emulation system 302 is communicatively coupled to sound processor 104. Emulation system 302 may be implemented by any suitable combination of hardware and software. For example, emulation system 302 may be implemented by a personal computer, a laptop computer, a mobile device (e.g., a smartphone or a tablet computer), a fitting device (e.g., a computing system located in a clinician's office and configured to fit cochlear implant systems to recipients), and/or any other suitable computing device as may serve a particular implementation.

Figure 4:
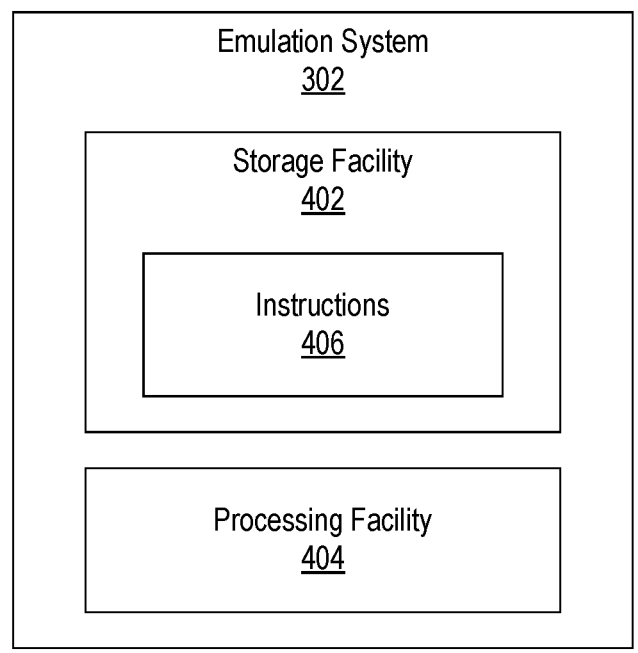
FIG. 4 illustrates components of an emulation system according to principles described herein.

FIG. 4 illustrates components of emulation system 302 that may be configured to perform any of the operations described herein. As shown, emulation system 302 may include, without limitation, a storage facility 402 and a processing facility 404 selectively and communicatively coupled to one another. Facilities 402 and 404 may each include or be implemented by hardware and/or software components (e.g., processors, memories, communication interfaces, instructions stored in memory for execution by the processors, etc.). In some examples, facilities 402 and 404 may be distributed between multiple devices and/or multiple locations as may serve a particular implementation. For examples, facilities 402 and 404 may be distributed between computing devices configured to communicate one with another by way of a network.

Storage facility 402 may maintain (e.g., store) executable data used by processing facility 404 to perform any of the operations described herein. For example, storage facility 402 may store instructions 406 that may be executed by processing facility 404 to perform any of the operations described herein. Instructions 406 may be implemented by any suitable application, software, code, and/or other executable data instance. In some examples, instructions 406 are implemented by an executable emulation application that may be configured to provide one or more remote listening environment emulation services and/or one or more hearing evaluation services. The emulation application may be provided by a manufacturer of a cochlear implant system, an entity associated with the remote listening environment (e.g., a manufacturer of a sound booth), and/or any other entity as may serve a particular implementation.

Storage facility 402 may maintain additional or alternative data received, generated, managed, used, and/or transmitted by processing facility 404 as may serve a particular implementation.

Processing facility 404 may be configured to perform (e.g., execute instructions 406 stored in storage facility 402 to perform) various remote listening environment emulation operations. For example, processing facility 404 may acoustically isolate a recipient of a cochlear implant system from the local listening environment by disabling a microphone included in the cochlear implant system, receive user input representative of a request to present a sound token to the recipient, generate a modified sound token, and present the modified sound token to the recipient while the microphone is disabled. These and other operations that may be performed by emulation system 302 will now be described.

During a hearing evaluation, it may be desirable to acoustically isolate the recipient from a local listening environment so that the cochlear implant system does not detect and present stimulation representative of sounds in the local listening environment to the recipient. As used herein, a local listening environment refers to an environment in which the recipient is physically located. For example, the local listening environment may be a room in which the user is physically located.

To acoustically isolate a recipient of a cochlear implant system from a local listening environment, emulation system 302 may disable a microphone included in the cochlear implant system. This may be performed in any suitable manner. For example, emulation system 302 may transmit a command to a sound processor of the cochlear implant system that directs the sound processor to turn off or otherwise disable any microphone that is connected to or part of the cochlear implant system.

Emulation system 302 may receive user input representative of a request to present a sound token to the recipient. This request may be received prior to or after the disabling of the microphone. The user input may be provided by the recipient, a clinician, and or any other user in any suitable manner. For example, emulation system 302 may present a graphical user interface (e.g., by displaying the graphical user interface on a display screen that is included in or connected to emulation system 302). The graphical user interface may present an option that may be selected by the user to provide the user input representative of the request to present the sound token to the recipient.

By way of illustration, emulation system 302 may facilitate selection, by way of a graphical user interface, of a file that includes data representative of the sound token. Once the file has been selected by a user, the user may select a "play" option displayed within the graphical user interface to direct emulation system 302 to begin presenting the sound token to the recipient.

The sound token may be represented by data included in an audio file stored locally by emulation system 302. Alternatively, the sound token may be represented by data included in a file maintained remotely by a server or other suitable computing device communicatively coupled to emulation system 302 by way of a network. In this implementation, the sound token may be presented to the recipient by streaming the sound token by way of the network.

In response to the user input, emulation system 302 may generate a modified sound token to more accurately emulate a remote listening environment. Emulation system 302 may generate the modified sound token a variety of different ways.

Figure 5A:
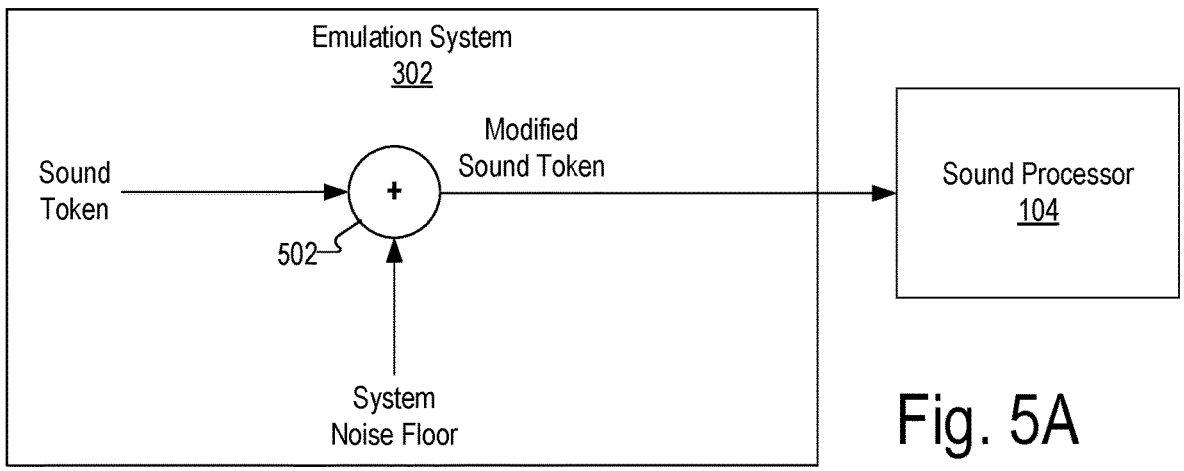
FIGS. 5A-5C show various processing operations that may be performed by an emulation system to generate a modified sound token according to principles described herein.
Figure 5B:
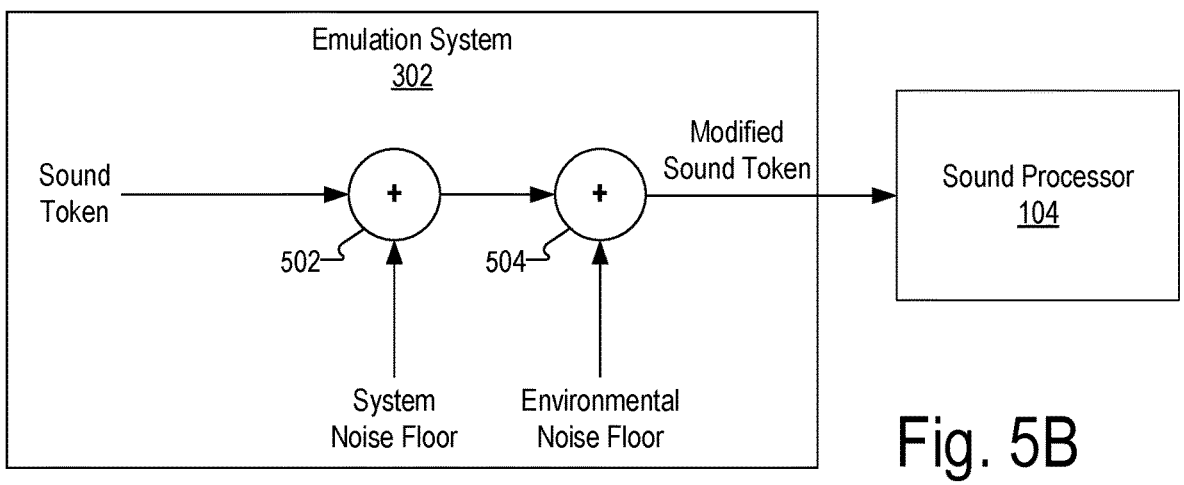
Figure 5C:
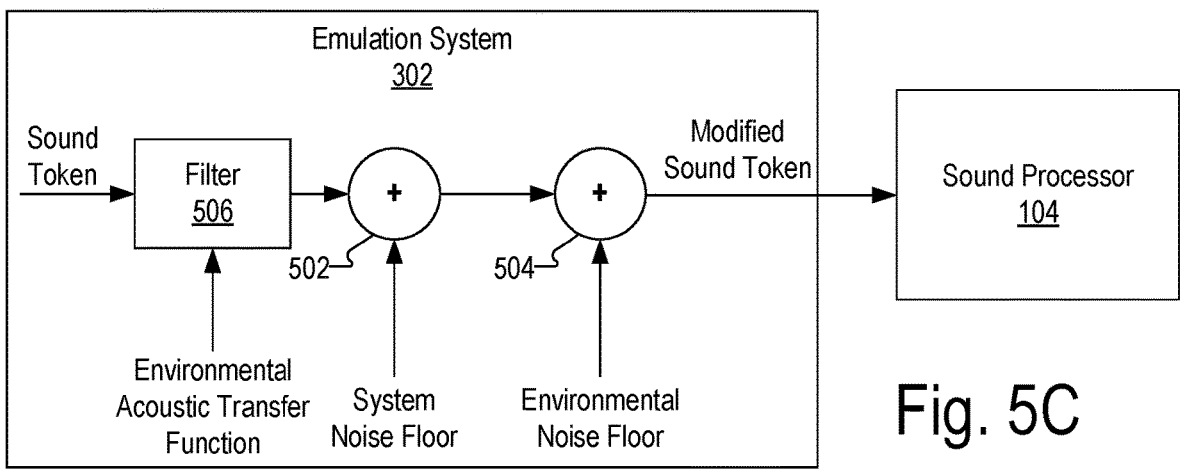

To illustrate, FIGS. 5A-5C show various processing operations that may be performed by emulation system 302 to generate a modified sound token for presentation to a recipient of the cochlear implant system. In FIG. 5A, emulation system 302 generates a modified sound token by adding a system noise floor of the cochlear implant system to the sound token. This addition is performed in FIG. 5A by summation block 502.

As used herein, a system noise floor of a cochlear implant system refers to noise generated by one or more components within the cochlear implant system itself while the microphone is enabled. This noise may be caused by components within the microphone, within the sound processor, within the headpiece, and/or any other component within the cochlear implant system and may be included in any signal output by the microphone while the microphone is enabled. One particular example of a system noise floor is a microphone noise floor of the microphone included in the cochlear implant system.

In some examples, the system noise floor is based on an actual measurement of the system noise floor. For example, emulation system 302 may transmit a command to the sound processor for the sound processor to perform a system noise floor measurement operation. This measurement operation may be performed in any suitable manner with respect to the microphone that is to be disabled. The sound processor may transmit data representative of the system noise floor to emulation system 302. Emulation system 302 may store the system noise floor data and add the system noise floor data to the sound token in any suitable manner. The system noise floor may alternatively be measured by any other suitable measurement device and/or technique as may serve a particular implementation.

Additionally or alternatively, the system noise floor may be based on a model of the system noise floor (e.g., any data that is not representative of an actual measurement of the noise floor of the specific cochlear implant used by the recipient). The model of the system noise floor may be generated and/or accessed by emulation system 302 in any suitable manner.

For example, emulation system 302 and/or any other computing device (e.g., a server) communicatively coupled to emulation system 302 may maintain a database of model system noise floors for a plurality of different types of cochlear implant systems (e.g., a plurality of different types of microphones. Accordingly, emulation system 302 may receive, by way of a graphical user interface, user input representative of one or more characteristics of the cochlear implant system. Such characteristics may include, but are not limited to, a cochlear implant system ID, a make and/or model of one or more components included in the cochlear implant system, and/or any other identifying information associated with the cochlear implant system. Additionally or alternatively, emulation system 302 may receive data representative of the one or more characteristics of the cochlear implant system directly from the sound processor (e.g., in response to a command transmitted by emulation system 302 to sound processor).

In response to receiving the data representative of the one or more characteristics of the cochlear implant system, emulation system 302 may query the database to identify data representative of a model system noise floor that corresponds to the cochlear implant system. This data may be used as the system noise floor for the cochlear implant system.

In FIG. 5B, emulation system 302 is further configured to modify the sound token by adding an environmental noise floor of the remote listening environment to the sound token. This addition is performed in FIG. 5B by summation block 504. While FIG. 5B shows that both the system noise floor and the environmental noise floor are added to the sound token, it will be recognized that in certain embodiments, only the environmental noise floor (and not the system noise floor) is added to the sound token.

As used herein, an environmental noise floor of a remote listening environment refers to background noise generated in any manner in the remote listening environment. For example, the environmental noise floor for a sound booth may be caused by electronics included in the sound booth.

In some examples, the environmental noise floor is based on an actual measurement of the noise floor of the remote listening environment. This measurement may be recorded by one or more microphones located within the remote listening environment. The environmental noise floor may alternatively be measured by any other suitable measurement device and/or technique as may serve a particular implementation. Data representative of the environmental noise floor may be transmitted to emulation system 302, which may store the environmental noise floor data and add the environmental noise floor data to the sound token in any suitable manner.

Additionally or alternatively, the environmental noise floor may be based on a model of the environmental noise floor (e.g., any data that is not representative of an actual measurement of the noise floor of the remote listening environment). The model of the environmental noise floor may be generated and/or accessed by emulation system 302 in any suitable manner.

For example, emulation system 302 and/or any other computing device (e.g., a server) communicatively coupled to emulation system 302 may maintain a database of model environmental noise floors for a plurality of different remote listening environments. Accordingly, emulation system 302 may receive, by way of a graphical user interface, user input representative of one or more characteristics of the remote listening environment. Such characteristics may include, but are not limited to, a remote listening environment ID, one or more room dimensions of the remote listening environment, one or more building materials of the remote listening environment, and/or any other identifying information associated with the remote listening environment.

In response to receiving the data representative of the one or more characteristics of the remote listening environment, emulation system 302 may query the database to identify data representative of a model environmental noise floor that corresponds to the remote listening environment. This data may be used as the environmental noise floor for the remote listening environment.

In FIG. 5C, emulation system 302 is further configured to modify the sound token by filtering the sound token with an acoustic transfer function of the remote listening environment. This filtering is performed in FIG. 5C by filter 506, which may be implemented in any suitable manner. While FIG. 5C shows that the sound token is modified by filtering the sound token with an acoustic transfer function of the remote listening environment and by adding the system noise floor and the environmental noise floor to the filtered sound token, it will be recognized that in certain embodiments, any combination of the operations shown in FIG. 5C may be performed.

As used herein, an acoustic transfer function of a remote listening environment represents one or more acoustic characteristics of the remote listening environment. Such acoustic characteristics include, but are not limited to, reverberation, attenuation, and/or other forms of audio distortion.

In some examples, the acoustic transfer function is based on an actual measurement of the acoustic transfer function of the remote listening environment. This measurement may be performed within the remote listening environment in any suitable manner. Data representative of the acoustic transfer function may be transmitted to emulation system 302, which may store the acoustic transfer function data and filter the sound token with the acoustic transfer function in any suitable manner.

Additionally or alternatively, the acoustic transfer function may be based on a model of the acoustic transfer function (e.g., any data that is not representative of an actual measurement of the acoustic transfer function of the remote listening environment). The model of the acoustic transfer function may be generated and/or accessed by emulation system 302 in any suitable manner.

For example, emulation system 302 and/or any other computing device (e.g., a server) communicatively coupled to emulation system 302 may maintain a database of model acoustic transfer functions for a plurality of different remote listening environments. Accordingly, emulation system 302 may receive, by way of a graphical user interface, user input representative of one or more characteristics of the remote listening environment. Such characteristics may include, but are not limited to, a remote listening environment ID, one or more room dimensions of the remote listening environment, one or more building materials of the remote listening environment, and/or any other identifying information associated with the remote listening environment.

In response to receiving the data representative of the one or more characteristics of the remote listening environment, emulation system 302 may query the database to identify data representative of a model acoustic transfer function that corresponds to the remote listening environment. This data may be used as the acoustic transfer function for the remote listening environment.

Figure 6:
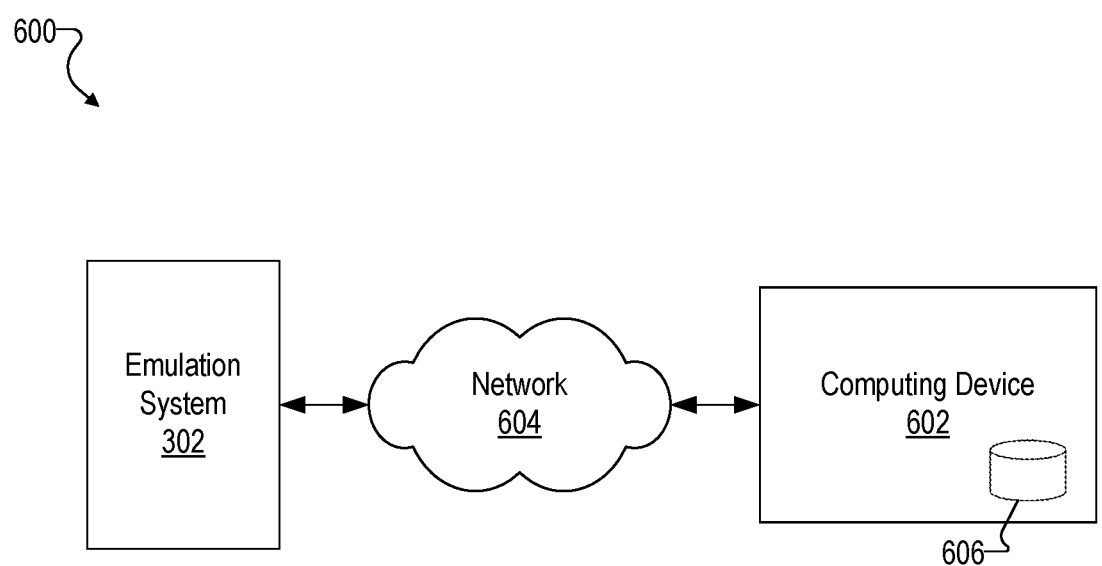
FIG. 6 illustrates an exemplary configuration in which an emulation system is connected to a computing device by way of a network according to principles described herein.

FIG. 6 illustrates an exemplary configuration 600 in which emulation system 302 is connected to a computing device 602 by way of a network 604. Network 604 may be implemented by any suitable network, such as the Internet, a wide area network, a local area network, a provider-specific wired or wireless network (e.g., a cable or satellite carrier network or a mobile telephone network), a content delivery network, and/or any other suitable network. Data may flow between emulation system 302 and computing device 602 using any communication technologies, devices, media, and protocols as may serve a particular implementation.

Computing device 602 may be implemented by one or more cloud-based computing devices configured to communicate with emulation system 302 by way of network 604. For example, computing device 602 may be implemented by one or more servers or other physical computing devices.

As shown, computing device 602 may maintain a database 606. Database 606 may be configured to include data that may be accessed by emulation system 302. For example, database 606 may include data representative of actual and/or model system noise floors, environmental noise floors, and/or acoustic transfer functions. Emulation system 302 may access the data included in database 606 in any suitable manner.

For example, emulation system 302 may transmit, to computing device 602 by way of network 604, an access request to access data representative of a system noise floor, an environmental noise floor, and/or an acoustic transfer function. In some examples, the access request is transmitted by emulation system 302 in response to emulation system 302 receiving a user request to present a sound token to a recipient of a cochlear implant system. In response to the access request, computing device 602 may retrieve the requested data from database 606 and transmit the requested data to emulation system 302 by way of network 304. Emulation system 302 may receive and use the requested data in any of the ways described herein.

Emulation system 302 may be further configured to generate, based on the presentation of the modified sound token to the recipient while the microphone is disabled, a hearing evaluation metric for the recipient. The hearing evaluation metric may be a hearing threshold metric, speech intelligibility test score, audibility test score, audiogram, and/or any other suitable metric as may serve a particular implementation. Emulation system 302 may process the hearing evaluation metric in any suitable manner. For example, emulation system 302 may present the hearing evaluation metric by way a graphical user interface. As another example, emulation system 302 may generate, based on the hearing evaluation metric, a command configured to adjust one or more operating parameters of the cochlear implant system. Emulation system 302 may then transmit the command to a sound processor of the cochlear implant system for execution.

Figure 7:
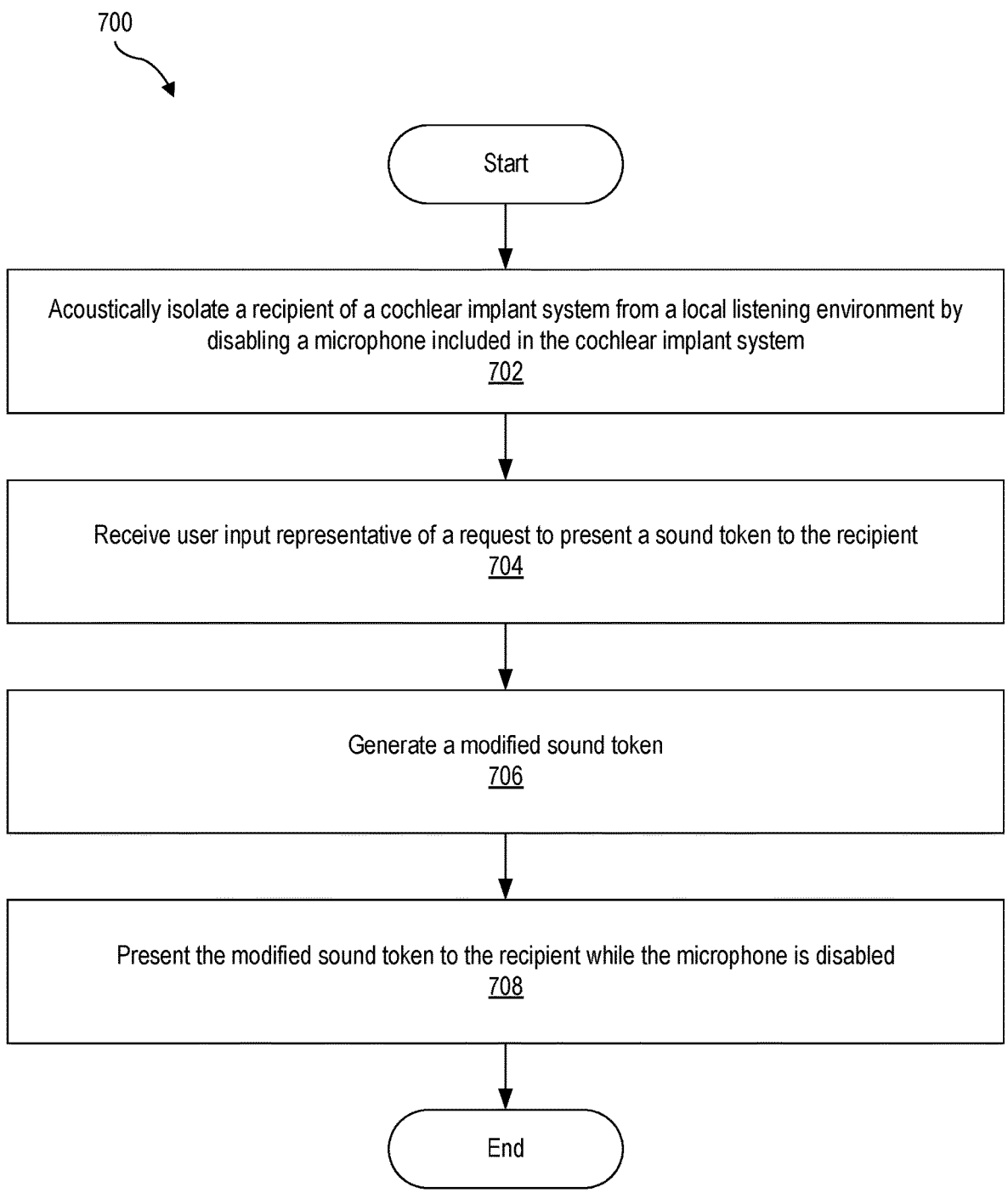
FIG. 7 illustrates an exemplary method according to principles described herein.

FIG. 7 illustrates an exemplary method 700 of emulating a remote listening environment for a recipient of a cochlear implant system. The operations shown in FIG. 7 may be performed by emulation system 302 and/or any implementation thereof. While FIG. 7 illustrates exemplary operations according to one embodiment, other embodiments may omit, add to, reorder, and/or modify any of the operations shown in FIG. 7.

In operation 702, an emulation system acoustically isolates the recipient of the cochlear implant system from a local listening environment by disabling a microphone included in the cochlear implant system. Operation 702 may be performed in any of the ways described herein.

In operation 704, the emulation system receives user input representative of a request to present a sound token to the recipient. Operation 704 may be performed in any of the ways described herein.

In operation 706, the emulation system generates a modified sound token. This may be performed in any of the ways described herein. For example, the emulation system may filter the sound token with an acoustic transfer function of the remote listening environment, add a system noise floor of the cochlear implant system to the sound token, and/or add an environmental noise floor of the remote listening environment to the sound token. Operation 706 may be performed in any of the ways described herein.

In operation 708, the emulation system presents the modified sound token to the recipient while the microphone is disabled. Operation 708 may be performed in any of the ways described herein.

In some examples, a non-transitory computer-readable medium storing computer-readable instructions may be provided in accordance with the principles described herein.

The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 8:
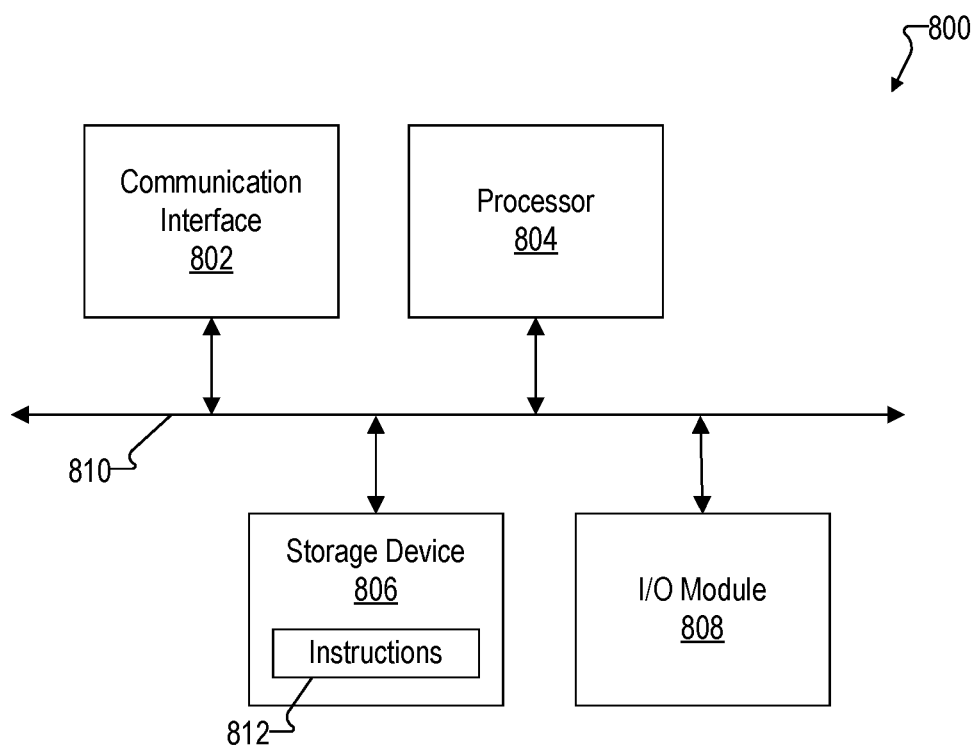
FIG. 8 illustrates an exemplary computing device according to principles described herein.

FIG. 8 illustrates an exemplary computing device 800 that may be specifically configured to perform one or more of the processes described herein. As shown in FIG. 8, computing device 800 may include a communication interface 802, a processor 804, a storage device 806, and an input/output ("I/O") module 808 communicatively connected one to another via a communication infrastructure 810. While an exemplary computing device 800 is shown in FIG. 8, the components illustrated in FIG. 8 are not intended to be limiting. Additional or alternative components may be used in other embodiments. Components of computing device 800 shown in FIG. 8 will now be described in additional detail.

Communication interface 802 may be configured to communicate with one or more computing devices. Examples of communication interface 802 include, without limitation, a wired network interface (such as a network interface card), a wireless network interface (such as a wireless network interface card), a modem, an audio/video connection, and any other suitable interface.

Processor 804 generally represents any type or form of processing unit capable of processing data and/or interpreting, executing, and/or directing execution of one or more of the instructions, processes, and/or operations described herein. Processor 804 may perform operations by executing computer-executable instructions 812 (e.g., an application, software, code, and/or other executable data instance) stored in storage device 806.

Storage device 806 may include one or more data storage media, devices, or configurations and may employ any type, form, and combination of data storage media and/or device. For example, storage device 806 may include, but is not limited to, any combination of the non-volatile media and/or volatile media described herein. Electronic data, including data described herein, may be temporarily and/or permanently stored in storage device 806. For example, data representative of computer-executable instructions 812 configured to direct processor 804 to perform any of the operations described herein may be stored within storage device 806. In some examples, data may be arranged in one or more databases residing within storage device 806.

I/O module 808 may include one or more I/O modules configured to receive user input and provide user output. I/O module 808 may include any hardware, firmware, software, or combination thereof supportive of input and output capabilities. For example, I/O module 808 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 808 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 808 is configured to provide graphical data to a display for presentation to a user. The graphical data may be representative of one or more graphical user interfaces and/or any other graphical content as may serve a particular implementation.

In some examples, any of the systems, computing devices, and/or other components described herein may be implemented by computing device 800. For example, storage facility 302 may be implemented by storage device 806, and processing facility 304 may be implemented by processor 804.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system for emulating a remote listening environment that is physically remote from a local listening environment in which a recipient of a cochlear implant system is located, the system comprising:
a memory storing instructions; and
a processor communicatively coupled to the memory and configured to execute the instructions to:
acoustically isolate the recipient from the local listening environment by disabling a microphone included in the cochlear implant system;
receive user input representative of a request to present a sound token to the recipient;
generate a modified sound token by adding a system noise floor of the cochlear implant system to the sound token, the system noise floor including a microphone noise floor of the microphone; and
present the modified sound token to the recipient while the microphone is disabled.

2. The system of claim 1, wherein the generating of the modified sound token further comprises adding an environmental noise floor of the remote listening environment to the sound token.

3. The system of claim 2, wherein the environmental noise floor is based on at least one of an actual measurement of a noise floor in the remote listening environment and a model of the remote listening environment.

4. The system of claim 2, wherein the processor is further configured to execute the instructions to:
transmit, to a computing device by way of a network in response to receiving the user input, an access request to access data representative of the environmental noise floor;
receive, from the computing device based on the access request, the data representative of the environmental noise floor; and use the data representative of the environmental noise floor to perform the adding of the environmental noise floor to the sound token.

5. The system of claim 2, the processor is further configured to execute the instructions to:
  receive, by way of a graphical user interface, user input representative of one or more characteristics of the remote listening environment; and
  determine, based on the user input representative of the one or more characteristics of the remote listening environment, the environmental noise floor.

6. The system of claim 1, wherein the processor is further configured to execute the instructions to:
  transmit, to a computing device by way of a network in response to receiving the user input, an access request to access data representative of the system noise floor;
  receive, from the computing device based on the access request, the data representative of the system noise floor; and
  use the data representative of the system noise floor to perform the adding of the system noise floor to the sound token.

7. The system of claim 1, the processor is further configured to execute the instructions to:
  receive, by way of a graphical user interface, user input representative of one or more characteristics of the cochlear implant system; and
  determine, based on the user input representative of the one or more characteristics of the cochlear implant system, the system noise floor.

8. The system of claim 1, wherein the presenting of the modified sound token to the recipient while the microphone is disabled comprises transmitting the modified sound token to the cochlear implant system by way of a direct audio input included in the cochlear implant system.

9. The system of claim 8, wherein the direct audio input comprises at least one of a direct audio input port included in a sound processor of the cochlear implant system and a wireless connection between the system and the sound processor.

10. The system of claim 1, the processor is further configured to execute the instructions to generate, based on the presenting of the modified sound token to the recipient while the microphone is disabled, a hearing evaluation metric for the recipient.

11. A method for emulating a remote listening environment that is physically remote from a local listening environment in which a recipient of a cochlear implant system is located, the method comprising:
  acoustically isolating, by an emulation system, the recipient from the local listening environment by disabling a microphone included in the cochlear implant system;
  receiving, by the emulation system, user input representative of a request to present a sound token to the recipient;
  generating, by the emulation system, a modified sound token by adding a system noise floor of the cochlear implant system to the sound token, the system noise floor including a microphone noise floor of the microphone; and
  presenting, by the emulation system, the modified sound token to the recipient while the microphone is disabled.

12. The method of claim 11, wherein the generating of the modified sound token further comprises adding an environmental noise floor of the remote listening environment to the sound token.

13. The method of claim 12, wherein the environmental noise floor is based on at least one of an actual measurement of a noise floor in the remote listening environment and a model of the remote listening environment.

* * * * *